United States Patent
Teillaud et al.

(10) Patent No.: US 11,439,605 B2
(45) Date of Patent: Sep. 13, 2022

(54) ADRENALINE PHARMACEUTICAL SOLUTION FOR AN INJECTION DEVICE

(71) Applicant: CROSSJECT, Dijon (FR)

(72) Inventors: Eric Teillaud, Daix (FR); Nicolas Baumard, Dijon (FR); Audrey Ressejeac, Saint Apollinaire (FR)

(73) Assignee: CROSSJECT, Dijon (FR)

( * ) Notice: Subject to any disclaimer, the term of this patent is extended or adjusted under 35 U.S.C. 154(b) by 0 days.

(21) Appl. No.: 17/604,124

(22) PCT Filed: Apr. 15, 2020

(86) PCT No.: PCT/EP2020/060523
§ 371 (c)(1),
(2) Date: Oct. 15, 2021

(87) PCT Pub. No.: WO2020/212381
PCT Pub. Date: Oct. 22, 2020

(65) Prior Publication Data
US 2022/0211643 A1 Jul. 7, 2022

(30) Foreign Application Priority Data

Apr. 18, 2019 (FR) ..................... 19/04166

(51) Int. Cl.
| | | |
|---|---|---|
| *A61K 31/137* | (2006.01) | |
| *A61K 9/00* | (2006.01) | |
| *A61K 47/10* | (2017.01) | |
| *A61P 9/04* | (2006.01) | |
| *A61K 47/18* | (2017.01) | |
| *A61K 9/08* | (2006.01) | |

(52) U.S. Cl.
CPC .......... *A61K 31/137* (2013.01); *A61K 9/0019* (2013.01); *A61K 9/08* (2013.01); *A61K 47/10* (2013.01); *A61K 47/183* (2013.01); *A61P 9/04* (2018.01)

(58) Field of Classification Search
CPC .... A61K 31/137; A61K 47/02; A61K 47/183; A61K 9/0019; A61K 9/08; Y02A 50/30
See application file for complete search history.

(56) References Cited

U.S. PATENT DOCUMENTS 10,130,592 B2 * 11/2018 Kannan .................. A61K 47/10

FOREIGN PATENT DOCUMENTS

| FR | 2779061 A1 | 12/1999 |
| FR | 3014317 A1 | 6/2015 |
| WO | 03/041687 A2 | 5/2003 |

OTHER PUBLICATIONS

Jul. 7, 2020 International Search Report issued in International Patent Application No. PCT/EP2020/060523.
Jul. 7, 2020 Written Opinion of the International Search Authority issued in International Patent Application No. PCT/EP2020/060523.

* cited by examiner

*Primary Examiner* — Savitha M Rao
(74) *Attorney, Agent, or Firm* — Oliff PLC

(57) ABSTRACT

An adrenaline pharmaceutical solution including at least: adrenaline or a pharmaceutically-acceptable salt thereof; vitamin E TPGS; a chelating agent; a solvent. The method also relates to its use in the treatment of anaphylactic shocks, cardiac arrests, asthma and cardiocirculatory distresses. The method also concerns an injection kit including an injection device and this pharmaceutical solution.

15 Claims, No Drawings

ADRENALINE PHARMACEUTICAL SOLUTION FOR AN INJECTION DEVICE

The invention concerns a pharmaceutical solution of adrenaline (also known as epinephrine) or of a pharmaceutically-acceptable salt thereof (hereinafter, abbreviated as «adrenaline pharmaceutical solution») intended to be injected by parenteral, in particular intramuscular, route.

Adrenaline is a hormone secreted by the central nervous system and also by the suprarenal glands. Strong emotions such as fear or anger result in the release of adrenaline into the bloodstream; which causes an increase in cardiac rate, muscle tension, arterial blood pressure, as well as sugar metabolism.

In medicine, the injection of adrenaline or adrenaline salts is known to be an appropriate treatment for cardiocirculatory arrests, anaphylactic shocks (related to an allergy) or some other serious states of shock.

For example, in case of an anaphylactic shock, the patient may inject adrenaline to himself intramuscularly with an injection device. Indeed, anaphylaxis is a sudden and severe generalized allergic reaction which may be fatal in just a few minutes in the absence of a proper treatment.

Adrenaline and the salts thereof belong to the catecholamines family.

Adrenaline, as well as salts thereof, are sensitive to oxidation. More specifically, adrenaline aqueous solutions deteriorate rapidly when exposed to air, light and/or heat. This degradation is visible as they fade into pink because of their oxidation into adrenochrome, then into brown with the formation of melamine.

That is why, because of this auto-oxidation of adrenaline, it is essential to implement appropriate steps that avoid the deterioration thereof. For example, it is known to store adrenaline solutions under suitable refrigeration in order to extend their shelf life.

It is further known to preserve adrenaline from auto-oxidation by combining it with an antioxidant. Many antioxidants have been used to stabilize adrenaline pharmaceutical solutions, including in particular injectable solutions. Amongst these antioxidants, mention may be made to sulphites (in particular metabisulphite), ascorbic acid, thioglycolate, thioglycerol, L-cysteine, propyl gallate, formaldehyde sulfoxylate, citric acid and monothioglycerol.

However, some of these antioxidants such as sulphite-based compounds (for example sodium metabisulphite or sodium bisulphite) may be the cause of severe allergic reactions. Furthermore, sodium bisulphite may react with adrenaline, thereby reducing the full potential of this active substance, and that by producing a by-product which is adrenaline sulfonic acid.

The development of long-life adrenaline pharmaceutical solutions is complex, because it is absolutely necessary to implement steps that take into account the fact that this active substance can easily oxidize in the presence of heat, air and/or light and that it can react with some antioxidants such as sulphites thereby reducing all of its treating potential.

The inventors of the present invention have looked at overcoming all these drawbacks detailed hereinabove and have developed a new pharmaceutical solution of adrenaline or of a pharmaceutically-acceptable salt thereof intended to be injected by parenteral, in particular intramuscular, route whose stability over time is improved in comparison with adrenaline solutions known in the prior art and which gets rid of sulphite-type antioxidants.

Surprisingly, the inventors of the present invention have discovered that the association of the antioxidant consisting of D-alpha-tocopheryl polyethylene glycol succinate (hereinafter, abbreviated as «vitamin E TPGS») with a chelating agent in a pharmaceutical solution of adrenaline or of a pharmaceutically-acceptable salt thereof allowed perfectly reaching these objectives.

Vitamin E TPGS is formed by esterification of D-alpha-tocopheryl acid succinate with polyethylene glycol (hereinafter, abbreviated as «PEG»).

Thus, a first object of the present invention is an adrenaline pharmaceutical solution comprising at least:
  adrenaline or a pharmaceutically-acceptable salt thereof;
  vitamin E TPGS;
  a chelating agent;
  a solvent.

The chelating agent may be selected from disodium ethylenediaminetetraacetate (also known as ethylenediaminetetraacetic acid disodium salt dehydrate and hereinafter, abbreviated as «disodium EDTA»), ethylenediaminetetraacetic acid and disodium calcium ethylenediaminetetraacetate.

Preferably, the chelating agent is disodium EDTA.

Surprisingly, the inventors of the present invention have discovered that the association of vitamin E TPGS with a chelating agent, preferably disodium EDTA, confers on the adrenaline solution a better stability over time compared to that of adrenaline solutions of the prior art. Indeed, the adrenaline solutions known in the prior art have expiry dates comprised between 18 and 21 months. The adrenaline solution according to the invention may have an expiry date longer than 24 months.

Hence, the present invention lies in the selection of an association of vitamin E TPGS and of a chelating agent (preferably, disodium EDTA) to stabilize an adrenaline pharmaceutical solution.

Indeed, it has been noticed through experiments that the pharmaceutical solutions according to the invention remained perfectly stable over time, and that even in severe storage conditions (namely, at a temperature of 40° C.). More specifically, in these storage conditions, unlike other comparable adrenaline solutions, it has been observed that:
  the adrenaline solutions according to the invention remained limpid and colorless;
  their pH remained almost unchanged, and
  the percentage of loss of purity was too low.

Hence, the inventors have noticed a synergetic effect between vitamin E TPGS and a chelating agent (preferably, disodium EDTA) which is based on the following facts:
  vitamin E TPGS avoids the degradation of adrenaline by auto-oxidation, whereas
  the chelating agent limits the decrease in the pH of said solution; which avoids chemical reactions within the solution that could also degrade adrenaline.

The pharmaceutically-acceptable salt of adrenaline may be chosen among adrenaline tartrate and adrenaline hydrochloride. It may be considered alone or in combination with the latter.

Preferably, the adrenaline salt is adrenaline tartrate.

The solvent may consist of any pharmaceutically-acceptable solvent that is compatible with adrenaline and salts thereof, as well as any other compound said pharmaceutical solution according to the invention comprises. It may consist of water, in particular water used in injection devices (in other words, water for injection preparation). Water for injection preparation is ultrapure and free of bacterial contaminants.

The pharmaceutical solution may further comprise at least one pH buffering agent. For example, it may consist of a pH buffering agent selected from hydrochloric acid and soda.

Advantageously, the pH of the pharmaceutical solution is comprised between 2.2 and 5, preferably between 3 and 3.8.

The pharmaceutical solution may further comprise at least one tonicity modifier. For example, it may consist of sodium chloride.

Said pharmaceutical solution may further comprise at least one pharmaceutically-acceptable excipient.

In an embodiment of the invention, the pharmaceutical solution comprises:
  adrenaline or a pharmaceutically-acceptable salt thereof;
  vitamin E TPGS;
  a chelating agent, preferably disodium EDTA;
  optionally, at least one pH buffering agent;
  optionally, at least one tonicity modifier;
  a solvent, preferably water for injection preparation.

Preferably, the pharmaceutical solution comprises:
  adrenaline or a pharmaceutically-acceptable salt thereof;
  vitamin E TPGS;
  disodium EDTA;
  optionally, soda or hydrochloric acid;
  optionally, sodium chloride;
  a solvent, preferably water for injection preparation.

More preferably, the pharmaceutical solution comprises:
  adrenaline tartrate;
  vitamin E TPGS;
  disodium EDTA;
  optionally, soda or hydrochloric acid;
  optionally, sodium chloride;
  a solvent, preferably water for injection preparation.

Advantageously, the adrenaline concentration in said pharmaceutical solution is comprised between 0.1 mg/mL and 1 mg/mL.

In some embodiments of the invention, the adrenaline concentration in said solution is 0.48 mg/mL or else 0.8 mg/mL.

The pharmaceutical solution according to the invention may comprise in mg for 1 mL of the solution:
  between 0.1 mg and 1 mg, more preferably between 0.48 and 0.8 mg, of adrenaline or of a pharmaceutically-acceptable salt thereof;
  between 0.1 mg and 20 mg, preferably between 2.5 mg and 15 mg, of vitamin E TPGS;
  between 0.1 mg and 2 mg, preferably between 1 mg and 1.5 mg, of a chelating agent;
  Q.S. 1 mL of solvent, preferably water for injection preparation. «Q.S.» standing for «Quantum Satis» means that the solvent shall be added in the mixture in a sufficient amount for the sum of the volumes of the constituents of the mixture being equal to 1 mL.

The pharmaceutical solution according to the invention may comprise in mg for 1 mL of the solution:
  between 0.1 mg and 1 mg, more preferably between 0.48 and 0.8 mg, of adrenaline or of a pharmaceutically-acceptable salt thereof;
  between 0.1 mg and 20 mg, preferably between 2.5 mg and 15 mg, of vitamin E TPGS;
  between 0.1 mg and 2 mg, preferably between 1 mg and 1.5 mg, of disodium EDTA;
  Q.S. 1 mL of solvent, preferably water for injection preparation.

Said solution may further comprise up to 10 mg of at least one pharmaceutically-acceptable excipient.

Another object of the present invention is a process for preparing a pharmaceutical solution according to the invention as described above comprising at least the following steps of:
  a) preparing, under stirring, a mixture comprising all of the constituents of said solution except adrenaline or the pharmaceutically-acceptable salt of adrenaline so as to dissolve them;
  b) dissolving adrenaline or a pharmaceutically-acceptable salt thereof in a solvent;
  c) adding to the mixture of step a), optionally under stirring, the dissolved adrenaline or the dissolved pharmaceutically-acceptable salt thereof.

Throughout the preparation process, the steps implementing a stirring are advantageously carried out at a stirring rate comprised between 200 and 400 rpm, more preferably between 250 and 300 rpm.

The method may be carried out under a nitrogen or argon atmosphere or else the mixture may be bubbled with nitrogen or argon.

Another object of the invention is the pharmaceutical solution as described hereinabove for its use in the treatment of anaphylactic shocks, cardiac arrests, asthma and cardio-circulatory distresses (in particular cardiocirculatory distresses with states of anaphylactic, hemorrhagic, traumatic shock, whether infectious or following a heart surgery). Preferably, it consists of the treatment of anaphylactic shocks.

Advantageously, said solution is in a form suitable for the administration by parenteral route, preferably by intramuscular route.

Another object of the present invention is an injection kit, preferably a kit for injection by intramuscular route, including:
  an injection device;
  the pharmaceutical solution according to the invention as described hereinabove.

Advantageously, the injection volume of the injection device is comprised between 0.3125 ml and 0.625 ml.

Said injection device may be intended for one single use. For example, it consists of a ready-to-use pre-filled tube.

In a preferred embodiment of the invention, said device is a pre-filled injection device which is disposable, needleless and automatic thanks to a gas generator equipping it. It may consist of a needleless injection device with a pyrotechnic cartridge. In this respect, the patent applications FR 2 815 544 A1 and FR 2 807 946 A1 describe an example of this injection device.

Quite advantageously, the injection device is a device commercialized by the company Crossject under the commercial name ZENEO®.

Thus, in one embodiment of the injection kit according to the invention, the injection device is a needleless injection device with a pyrotechnic cartridge.

EXPERIMENTAL PART

Experiments have been carried out in order to compare the stability of adrenaline pharmaceutical solutions according to the invention with that of comparable pharmaceutical solutions which were free of any antioxidant or which comprised antioxidants known in the prior art to stabilize the adrenaline pharmaceutical solutions, possibly also with a chelating agent which was disodium EDTA.

More specifically, the following 19 adrenaline solutions have been prepared:

solutions S1 and S2: 2 adrenaline solutions according to the invention;

solutions C1 and C2: 2 comparable adrenaline solutions which were free of any antioxidant;

solutions C3 and C4: 2 comparable adrenaline solutions which contained vitamin E TPGS as an antioxidant but were free of any chelating agent;

solutions C5 to C11: 7 comparable adrenaline solutions which contained one or several antioxidant(s) other than vitamin E TPGS and which were free of any chelating agent;

solutions C12 to C17: 5 comparable adrenaline solutions which contained one or several antioxidant(s) other than vitamin E TPGS, as well as a chelating agent.

All of the 19 solutions have been prepared as follows:

First of all, in the context of this preparation of 19 solutions, water for injectable solution that has been used has been subjected to bubbling with dinitrogen for 12 hours in order to suppress any trace of residual dioxygen (such that its content is lower than 0.5 ppm).

All of the constituents except the active substance (namely, adrenaline or adrenaline tartrate) have been mixed together in a 200 mL vial.

Afterwards, water for injection preparation has been added in the vial until obtaining a volume of 180 mL.

The solution thus obtained has been stirred with a magnetic stirrer so that all of the constituents are dissolved.

The pH has been adjusted to a value of 3.4 with a soda (NaOH) or hydrochloric acid (HCl) solution at a concentration of 1 mol/L. These solutions have been subjected beforehand to bubbling with dinitrogen.

The volume of the solution has been completed to 200 mL with water of injection preparation. Thus, a $1^{st}$ solution is obtained.

Afterwards, about 1 mL of this $1^{st}$ solution has been used to dissolve adrenaline or, where appropriate, adrenaline tartrate in a vial.

The adrenaline solution thus obtained has been transferred into a 100 mL vial.

The vial in which adrenaline has been dissolved has been rinsed several times with small volumes (about 1 mL) of the $1^{st}$ solution, and then this rinsing solution has been transferred into the 100 mL vial, so as to recover the entirety of adrenaline present in the vial.

Finally, on completion of these rinsings, the volume has been completed to 100 mL with the $1^{st}$ solution.

The 19 adrenaline solutions thus obtained were all limpid and colorless.

In Tables 1 to 3 hereinbelow, «Q.S.» stands for «Quantum Satis» meaning that:
- the added amount of soda or hydrochloric acid at a concentration of 1 mol/L was such that the pH has been adjusted to about 3.4;
- the amount of water was such that the volume of the solution has been completed to 100 mL.

Table 1 hereinbelow details the amounts of each of the constituents of the solutions S1, S2, C1 to C4 for a volume of 1 mL of each of these solutions.

TABLE 1

| Constituents | S1 | S2 | C1 | C2 | C3 | C4 |
|---|---|---|---|---|---|---|
| Adrenaline (mg) | 0 | | 0.6 | | 0 | |
| Adrenaline tartrate (mg) | 1.60 (equivalent to 0.88 of adrenaline) | | 0 | | 1.09 (equivalent to 0.6 of adrenaline) | |
| NaCl (mg) | 6 | | 8 | | 6 | |

TABLE 1-continued

| Constituents | S1 | S2 | C1 | C2 | C3 | C4 |
|---|---|---|---|---|---|---|
| Vitamin E TPGS (mg) | 11 | 15 | 0 | | 7.5 | 3 |
| Disodium EDTA (mg) | | 1.5 | | | 0 | |
| NaOH or HCl | Q.S. pH of 3.4 | | | | | |
| Water | Q.S. 1 mL | | | | | |

Table 1 detailing the amounts of each of the constituents of the solutions S1, S2 and C1 to C4

Table 2 hereinbelow details the amounts of each of the constituents of the solutions C5 to C11 for a volume of 1 mL of each of these solutions.

TABLE 2

| Constituents | C5 | C6 | C7 | C8 | C9 | C10 | C11 |
|---|---|---|---|---|---|---|---|
| Adrenaline (mg) | 0.88 | | | 0 | | | |
| Adrenaline tartrate (mg) | 0 | 1.09 (equivalent to 0.6 of adrenaline) | | | | | |
| NaCl (mg) | | | | 6 | | | |
| Sodium metabisulphite (mg) | 1.7 | 1 | 0.5 | 0 | | | |
| L-cysteine (mg) | | 0 | | 1 | 0 | 0 | 0 |
| Citric acid (mg) | | | | 0 | 3 | 0 | 3 |
| Monothioglycerol (mg) | | | | 0 | 0 | 10 | 10 |
| NaOH or HCl | Q.S. pH of 3.4 | | | | | | |
| Water | Q.S. 1 mL | | | | | | |

Table 2 detailing the amounts of each of the constituents of the solutions C5 to C11

Table 3 hereinbelow details the amounts of each of the constituents of the solutions C12 to C17 for a volume of 1 mL of each of these solutions.

TABLE 3

| Constituents | C12 | C13 | C14 | C15 | C16 | C17 |
|---|---|---|---|---|---|---|
| Adrenaline tartrate (mg) | 1.09 (equivalent to 0.6 of adrenaline) | | 1.60 (equivalent to 0.88 of adrenaline) | 1.09 (equivalent to 0.6 of adrenaline) | | |
| NaCl (mg) | | | | 6 | | |
| Sodium metabisulphite (mg) | 1 | 1.5 | 2 | 0 | | |
| L-cysteine (mg) | | 0 | | 1 | | |
| Citric acid (mg) | | | | 0 | 3 | |
| Monothioglycerol (mg) | | | | 0 | 0 | 10 |
| Disodium EDTA (mg) | 1 | | 1.5 | | 1 | |
| NaOH or HCl | Q.S. pH of 3.4 | | | | | |
| Water | Q.S. 1 mL | | | | | |

Table 3 detailing the amounts of each of the constituents of the solutions C12 to C17

The stability of these 19 adrenaline solutions has been determined over time (namely up to 3 months), and at different storage temperatures: 25° C., 40° C. and 60° C.

Tables 4 to 10 hereinbelow detail, as a function of time and storage temperature, for the solutions S1, S2 and C1 to C17:
- the pH of the solution;
- the appearance of the solution;
- the percentage of loss of purity of adrenaline in the considered solution.

The percentage of loss of purity of adrenaline in the considered solution has been determined by high-performance liquid chromatography coupled with an ultraviolet detection according to the method detailed in the adrenaline tartrate monograph No. 01/2008:0254 derived from the 9th edition of European Pharmacopoeia.

TABLE 4

Table 4 detailing the stability parameters of the solutions S1 and S2

| Solution | | | Appearance | pH | % of loss of purity |
|---|---|---|---|---|---|
| S1 | T0 | | Limpid and colorless | 3.37 | — |
| | 1 month | 25° C. | Limpid and colorless | 3.47 | 0 |
| | | 40° C. | Limpid and colorless | 3.47 | 0 |
| | | 60° C. | brown | 3.39 | 10.0 |
| | 2 months | 25° C. | Limpid and colorless | 3.45 | 0 |
| | | 40° C. | Limpid and colorless | 3.45 | 0.1 |
| | 3 months | 25° C. | Limpid and colorless | 3.43 | 0 |
| | | 40° C. | Limpid and colorless | 3.43 | 0.6 |
| S2 | T0 | | Limpid and colorless | 3.37 | — |
| | 1 month | 25° C. | Limpid and colorless | 3.47 | 0 |
| | | 40° C. | Limpid and colorless | 3.45 | 0 |
| | | 60° C. | brown | 3.40 | 6.5 |
| | 2 months | 25° C. | Limpid and colorless | 3.44 | 0 |
| | | 40° C. | Limpid and colorless | 3.42 | 0.1 |
| | 3 months | 25° C. | Limpid and colorless | 3.41 | 0 |
| | | 40° C. | Limpid and colorless | 3.42 | 0.3 |

In light of Table 4, it is observed that the solutions S1 and S2 according to the invention remain stable over time, and that under severe temperature conditions. Indeed, the solutions S1 and S2 start fading at a temperature of 60° C., namely at a high temperature. Are also noticed the very low percentages of loss of purity, except for the very high temperature of 60° C. Furthermore, it is noticed that the pH of the solutions S1 and S2 remains almost unchanged, and that even at 60° C.

These experimental results demonstrate the excellent stability of the adrenaline solutions according to the invention.

TABLE 5

Table 5 detailing the stability parameters of the solutions C1 and C2

| Solution | | | Appearance | pH | % of loss of purity |
|---|---|---|---|---|---|
| C1 | T0 | — | Limpid and colorless | 3.43 | — |
| | 2 weeks | 60° C. | Dark maroon | 2.93 | 21.0 |
| | 1 month | 25° C. | Amber | 3.75 | 4.5 |
| | | 40° C. | Amber | 3.21 | 8.3 |
| C2 | T0 | | Limpid and colorless | 3.43 | — |
| | 2 weeks | 60° C. | Maroon | 3.11 | 26.6 |
| | 1 month | 25° C. | Limpid and colorless | 3.42 | 1.8 |
| | | 40° C. | Orange | 3.28 | 13.9 |

In light of Table 5, these tests with the solutions C1 and C2 demonstrate that the adrenaline solutions free of any antioxidant are not stable over time. Indeed, the solutions C1 and C2 became colored quickly and the percentage of loss of purity increases over time.

TABLE 6

Table 6 detailing the stability parameters of the solutions C3 and C4

| Solution | | | Appearance | pH | % of loss of purity |
|---|---|---|---|---|---|
| C3 | T0 | — | Limpid and colorless | 3.43 | — |
| | 2 weeks | 60° C. | Slightly yellow | 3.36 | 12.5 |
| | 1 month | 25° C. | Limpid and colorless | 3.40 | 3.8 |
| | | 40° C. | Limpid and colorless | 3.36 | 6.3 |
| | | 60° C. | Maroon | 3.30 | 25.9 |
| | 2 months | 25° C. | Limpid and colorless | 3.42 | 3.9 |
| | | 40° C. | Limpid and colorless | 3.39 | 8.9 |
| | 3 months | 25° C. | Limpid and colorless | 3.41 | 4.5 |
| | | 40° C. | Limpid and colorless | 3.41 | 11.6 |
| C4 | T0 | | Limpid and colorless | 3.39 | — |
| | 2 weeks | 60° C. | Dark maroon | 3.08 | 32.6 |
| | 1 month | 25° C. | Slightly yellow | 3.40 | 2.6 |
| | | 40° C. | Amber | 3.27 | 14.8 |

In light of Table 6, these tests with the solutions C3 and C4 demonstrate that the adrenaline solutions comprising vitamin E TPGS but which are free of any chelating agent have a percentage of loss of purity which increases over time and with temperature. These solutions C3 and C4 are less stable than the solutions S1 and S2 according to the invention.

TABLE 7

Table 7 detailing the stability parameters of the solutions C5 to C7

| Solution | | | Appearance | pH | % of loss of purity |
|---|---|---|---|---|---|
| C5 | T0 | — | Limpid and colorless | 3.43 | — |
| | 1 month | 25° C. | Limpid and colorless | 3.00 | 2.8 |
| | | 40° C. | Limpid and colorless | 2.63 | 8.4 |
| | | 60° C. | Limpid and colorless | 2.73 | 25.3 |
| | 2 months | 25° C. | Limpid and colorless | 2.90 | 4.4 |
| | | 40° C. | Limpid and colorless | 2.78 | 13.2 |
| | 3 months | 25° C. | Limpid and colorless | 2.82 | 5.2 |
| | | 40° C. | Limpid and colorless | 2.61 | 15.3 |
| C6 | T0 | — | Limpid and colorless | 3.38 | — |
| | 2 weeks | 60° C. | Slightly yellow | 2.27 | 13 |
| | 1 month | 25° C. | Limpid and colorless | 3.34 | 1 |
| | | 40° C. | Limpid and colorless | 2.76 | 8 |
| | | 60° C. | Amber | 2.29 | 20 |
| | 2 months | 25° C. | Limpid and colorless | 3.19 | 2.5 |
| | | 40° C. | Limpid and colorless | 2.60 | 10.7 |
| | 3 months | 25° C. | Limpid and colorless | 3.08 | 4.9 |

TABLE 7-continued

Table 7 detailing the stability parameters of the solutions C5 to C7

| Solution | | | Appearance | pH | % of loss of purity |
|---|---|---|---|---|---|
| | | 40° C. | Limpid and colorless | 2.54 | 13.8 |
| C7 | T0 | — | Limpid and colorless | 3.41 | — |
| | 2 weeks | 60° C. | Orange | 2.56 | 10.3 |
| | 1 month | 25° C. | Limpid and colorless | 3.34 | 1.6 |
| | | 40° C. | Limpid and colorless | 2.94 | 6.9 |
| | | 60° C. | Amber | 2.55 | 25.1 |
| | 2 months | 25° C. | Limpid and colorless | 3.25 | 1.6 |
| | | 40° C. | Limpid and colorless | 2.79 | 8.1 |
| | 3 months | 25° C. | Limpid and colorless | 3.17 | 3.3 |
| | | 40° C. | Limpid and colorless | 2.73 | 10.2 |

In light of Table 7, these tests with the solutions C5 to C7 demonstrate that the adrenaline solutions comprising sodium metabisulphite as an antioxidant have a percentage of loss of purity which increases over time and with temperature.

Furthermore, it is noticed that the pH varies over time and with the increase in temperature. These solutions C5 to C7 are not stable over time.

TABLE 8

Table 8 detailing the stability parameters of the solutions C8 to C11

| Solution | | | Appearance | pH | % of loss of purity |
|---|---|---|---|---|---|
| C8 | T0 | — | Limpid and colorless | 3.43 | — |
| | 2 weeks | 60° C. | Orange | 3.40 | 27.7 |
| | 1 month | 25° C. | Slightly yellow | 3.38 | 18.9 |
| | | 40° C. | Yellow | 3.32 | 30.0 |
| | | 60° C. | Orange | 3.39 | 41.0 |
| C9 | T0 | — | Limpid and colorless | 3.43 | — |
| | 2 weeks | 60° C. | Dark maroon | 3.31 | 24.3 |
| | 1 month | 25° C. | Slightly pink | 3.40 | 7.1 |
| | | 40° C. | Orange | 3.36 | 11.1 |
| C10 | T0 | — | Limpid and colorless | 3.44 | — |
| | 2 weeks | 60° C. | Slightly yellow | 3.21 | 63.4 |
| | 1 month | 25° C. | Slightly yellow | 3.28 | 62.5 |
| | | 40° C. | Slightly yellow | 3.19 | 65.4 |
| | | 60° C. | Slightly yellow | 3.23 | 81.7 |
| C11 | T0 | — | Limpid and colorless | 3.40 | — |
| | 2 weeks | 60° C. | Limpid and colorless | 3.31 | 52.8 |
| | 1 month | 25° C. | Limpid and colorless | 3.33 | 52.5 |
| | | 40° C. | Limpid and colorless | 3.33 | 58.0 |
| | | 60° C. | Limpid and colorless | 3.34 | 76.9 |

In light of Table 8, these tests with the solutions C8 to C11 demonstrate that the adrenaline solutions comprising L-cysteine, citric acid or monothioglycerol as an antioxidant have a percentage of loss of purity which increases over time and with temperature. Furthermore, it is noticed that the solutions become colored very quickly. These solutions C8 to C11 are not stable over time.

TABLE 9

Table 9 detailing the stability parameters of the solutions C12 to C14

| Solution | | | Appearance | pH | % of loss of purity |
|---|---|---|---|---|---|
| C12 | T0 | — | Limpid and colorless | 3.40 | — |
| | 2 weeks | 60° C. | Limpid and colorless | 2.62 | 14.4 |
| | 1 month | 25° C. | Limpid and colorless | 3.36 | 0.8 |
| | | 40° C. | Limpid and colorless | 3.16 | 5.0 |
| | | 60° C. | Limpid and colorless | 2.50 | 15.9 |
| | 2 months | 25° C. | Limpid and colorless | 3.34 | 0.7 |
| | | 40° C. | Limpid and colorless | 3.08 | 7.6 |
| | 3 months | 25° C. | Limpid and colorless | 3.29 | 2.0 |
| | | 40° C. | Limpid and colorless | 3.11 | 11.8 |
| C13 | T0 | — | Limpid and colorless | 3.42 | — |
| | 1 month | 25° C. | Limpid and colorless | 3.47 | 0.9 |
| | | 40° C. | Limpid and colorless | 3.30 | 5.5 |
| | | 60° C. | Limpid and colorless | 3.03 | 25.7 |
| | 2 months | 25° C. | Limpid and colorless | 3.42 | 2.0 |
| | | 40° C. | Limpid and colorless | 3.23 | 10.8 |
| | 3 months | 25° C. | Limpid and colorless | 3.42 | 2.6 |
| | | 40° C. | Limpid and colorless | 2.99 | 14.0 |
| C14 | T0 | — | Limpid and colorless | 3.42 | — |
| | 1 month | 25° C. | Limpid and colorless | 3.42 | 1.1 |
| | | 40° C. | Limpid and colorless | 3.29 | 5.9 |
| | | 60° C. | Maroon | 3.55 | 29.3 |
| | 2 months | 25° C. | Limpid and colorless | 3.40 | 2.2 |
| | | 40° C. | Limpid and colorless | 3.26 | 10.5 |
| | 3 months | 25° C. | Limpid and colorless | 3.36 | 2.8 |
| | | 40° C. | Limpid and colorless | 3.32 | 13.6 |

In light of Table 9, these tests with the solutions C12 to C14 demonstrate that the adrenaline solutions comprising sodium metabisulphite as an antioxidant in combination with a chelating agent which is disodium EDTA have a higher percentage of loss of purity than that of the solutions S1 and S2 over time and with the increase in temperature. Furthermore, it is noticed that the pH varies over time and with the increase in temperature for the solutions C12 to C14; which is not the case with the solutions S1 and S2. Hence, these solutions C12 to C14 are less stable over time than the solutions S1 and S2.

TABLE 10

Table 10 detailing the stability parameters of the solutions C15 to C17

| Solution | | | Appearance | pH | % of loss of purity |
|---|---|---|---|---|---|
| C15 | T0 | — | Limpid and colorless | 3.40 | — |

TABLE 10-continued

Table 10 detailing the stability parameters of the solutions C15 to C17

| Solution | | | Appearance | pH | % of loss of purity |
|---|---|---|---|---|---|
| | 2 weeks | 60° C. | Limpid and colorless | 3.37 | 40.0 |
| | 1 month | 25° C. | Limpid and colorless | 3.39 | 8.2 |
| | | 40° C. | Limpid and colorless | 3.37 | 9.9 |
| | | 60° C. | Orange | 3.42 | 49.6 |
| C16 | T0 | — | Limpid and colorless | 3.35 | — |
| | 2 weeks | 60° C. | Limpid and colorless | 3.36 | 36.9 |
| | 1 month | 25° C. | Limpid and colorless | 3.38 | 10.6 |
| | | 40° C. | Limpid and colorless | 3.37 | 19.5 |
| | | 60° C. | Maroon | 3.41 | 48.2 |
| C17 | T0 | — | Limpid and colorless | 3.37 | — |
| | 2 weeks | 60° C. | Limpid and colorless | 3.26 | 54.5 |
| | 1 month | 25° C. | Limpid and colorless | 3.32 | 51.9 |
| | | 40° C. | Limpid and colorless | 3.29 | 55.8 |
| | | 60° C. | Limpid and colorless | 3.29 | 79.5 |

In light of Table 10, these tests with the solutions C15 to C17 demonstrate that the adrenaline solutions comprising L-cysteine, citric acid and monothioglycerol as an antioxidant in combination with a chelating agent which is disodium EDTA have a much higher percentage of loss of purity than that of the solutions S1 and S2 after only one month of storage. This increase in the percentage of loss of purity increases with the increase in temperature. Hence, these solutions C15 to C17 are significantly less stable over time than the solutions S1 and S2.

The invention claimed is:

1. An adrenaline pharmaceutical solution comprising at least:
   adrenaline or a pharmaceutically-acceptable salt thereof;
   D-alpha-tocopheryl polyethylene glycol succinate (hereinafter, abbreviated as «vitamin E TPGS»);
   a chelating agent;
   a solvent.

2. The pharmaceutical solution according to claim 1, wherein the pharmaceutically-acceptable salt of adrenaline is selected from adrenaline tartrate and adrenaline hydrochloride.

3. The pharmaceutical solution according to claim 2, wherein the pharmaceutically-acceptable salt of adrenaline is adrenaline tartrate.

4. The pharmaceutical solution according to claim 1, wherein the chelating agent is selected from disodium ethylenediaminetetraacetate (hereinafter, abbreviated as «disodium EDTA»), ethylenediaminetetraacetic acid and disodium calcium ethylenediaminetetraacetate.

5. The pharmaceutical solution according to claim 4, wherein the chelating agent is disodium EDTA.

6. The pharmaceutical solution according to claim 1, wherein it further comprises at least one pH buffering agent which is selected from hydrochloric acid and soda.

7. The pharmaceutical solution according to claim 1, wherein the pH of the pharmaceutical solution is comprised between 2.2 and 5.

8. The pharmaceutical solution according to claim 1, wherein it further comprises at least one tonicity modifier which is sodium chloride.

9. The pharmaceutical solution according to claim 1, wherein the adrenaline concentration in said pharmaceutical solution is comprised between 0.1 mg/mL and 1 mg/ml.

10. The pharmaceutical solution according to claim 1, wherein it comprises in mg for 1 mL of the solution:
    between 0.1 mg and 1 mg of adrenaline or of a pharmaceutically-acceptable salt thereof;
    between 0.1 mg and 20 mg of vitamin E TPGS;
    between 0.1 mg and 2 mg of a chelating agent;
    Q.S. 1 mL of solvent.

11. A process for preparing the pharmaceutical solution according to claim 1, wherein it comprises at least the following steps of:
    a) preparing, under stirring, a mixture comprising all of the constituents of said solution except adrenaline or the pharmaceutically-acceptable salt of adrenaline so as to dissolve them;
    b) dissolving adrenaline or a pharmaceutically-acceptable salt thereof in a solvent;
    c) adding to the mixture of step a) the dissolved adrenaline or the dissolved pharmaceutically-acceptable salt thereof.

12. A pharmaceutical solution according to claim 1 for its use in the treatment of anaphylactic shocks, cardiac arrests, asthma and cardiocirculatory distresses.

13. The pharmaceutical solution according to claim 12, wherein said solution is in a form suitable for the administration by parenteral route.

14. An injection kit including:
    an injection device;
    the pharmaceutical solution according to claim 1.

15. The injection kit according to claim 14, wherein the injection device is a needleless injection device with a pyrotechnic cartridge.

* * * * *